United States Patent
Schutte et al.

(10) Patent No.: US 12,195,711 B1
(45) Date of Patent: Jan. 14, 2025

(54) DRAWER SYSTEM FOR CULTIVATING TISSUE

(71) Applicant: Humacyte, Inc., Durham, NC (US)

(72) Inventors: Robert Schutte, Cary, NC (US); Dustin Cashman, Chapel Hill, NC (US); Joshua McCall, Seattle, WA (US); Heather L Prichard, Wake Forest, NC (US); Justin T. Strader, Durham, NC (US)

(73) Assignee: Humacyte, Inc., Durham, NC (US)

( * ) Notice: Subject to any disclaimer, the term of this patent is extended or adjusted under 35 U.S.C. 154(b) by 0 days.

(21) Appl. No.: 16/875,902

(22) Filed: May 15, 2020

Related U.S. Application Data

(60) Provisional application No. 62/849,485, filed on May 17, 2019.

(51) Int. Cl.
| | | |
|---|---|---|
| C12M 1/00 | (2006.01) | |
| C12M 1/12 | (2006.01) | |
| C12M 1/34 | (2006.01) | |
| C12M 1/36 | (2006.01) | |
| C12M 3/04 | (2006.01) | |
| C12M 3/06 | (2006.01) | |

(52) U.S. Cl.
CPC ............ *C12M 23/58* (2013.01); *C12M 23/04* (2013.01); *C12M 27/12* (2013.01); *C12M 27/16* (2013.01); *C12M 41/12* (2013.01); *C12M 41/40* (2013.01); *C12M 41/48* (2013.01)

(58) Field of Classification Search
CPC ...... C12M 23/04; C12M 41/48; C12M 23/58; C12M 41/12; C12M 41/14; C12M 41/16; C12M 27/12; C12M 27/16; C12M 41/40
See application file for complete search history.

(56) References Cited

U.S. PATENT DOCUMENTS

| | | |
|---|---|---|
| 3,388,574 A | 6/1968 | Vincent |
| 3,606,596 A | 9/1971 | Edwards |
| 4,519,754 A | 5/1985 | Minick |
| 4,925,376 A | 5/1990 | Kahler |

(Continued)

FOREIGN PATENT DOCUMENTS

| | | | |
|---|---|---|---|
| CN | 201406422 | * | 2/2010 |
| CN | 108440045 | * | 8/2018 |

(Continued)

OTHER PUBLICATIONS

Discussion of servomotors and braking systems. ResearchGate. 2013. Retrieved Dec. 11, 2021. (Year: 2013).*

(Continued)

*Primary Examiner* — Holly Kipouros
*Assistant Examiner* — Nathan G Esperon
(74) *Attorney, Agent, or Firm* — COOLEY LLP

(57) ABSTRACT

Embodiments of the present disclosure are directed to systems, apparatuses, devices and methods for a bioreactor which, in some embodiments, comprises a drawer cage, housing or frame (such terms being used interchangeably throughout), at least one drawer arranged within the drawer cage, where each drawer can be configured to contain a plurality of bioreactors for cultivating biological matter, and a platform upon which the drawer cage is positioned. The platform can include a first axis upon which the drawer cage rotates or tilts thereon.

26 Claims, 6 Drawing Sheets

(56) References Cited

U.S. PATENT DOCUMENTS

| | | | |
|---|---|---|---|
| 5,447,417 A | 9/1995 | Kuhl et al. | |
| 5,470,744 A * | 11/1995 | Astle | C12M 41/14 160/241 |
| 5,547,329 A * | 8/1996 | Hirai | C12M 23/48 53/251 |
| 5,823,930 A | 10/1998 | Runge et al. | |
| 6,129,428 A * | 10/2000 | Helwig | F25D 25/04 312/305 |
| 6,475,776 B1 * | 11/2002 | Higuchi | C12M 27/10 422/561 |
| 7,878,786 B2 | 2/2011 | Yost et al. | |
| 10,085,829 B2 | 10/2018 | Soletti et al. | |
| 11,959,060 B1 | 4/2024 | Prichard et al. | |
| 2004/0219659 A1 | 11/2004 | Altman et al. | |
| 2004/0241835 A1 * | 12/2004 | Hutmacher | C12M 41/32 435/298.2 |
| 2005/0009178 A1 | 1/2005 | Yost et al. | |
| 2005/0069401 A1 * | 3/2005 | Malin | C12M 41/48 414/277 |
| 2005/0084955 A1 * | 4/2005 | Tamaoki | G01N 35/025 435/286.2 |
| 2008/0032278 A1 | 2/2008 | Jones | |
| 2008/0220506 A1 | 9/2008 | Yost et al. | |
| 2008/0234806 A1 | 9/2008 | Dancu | |
| 2009/0042293 A1 * | 2/2009 | Hata | C12M 23/58 382/133 |
| 2010/0105138 A1 | 4/2010 | Dodd et al. | |
| 2011/0207209 A1 | 8/2011 | Hammons et al. | |
| 2011/0319823 A1 | 12/2011 | Bojan et al. | |
| 2012/0028234 A1 | 2/2012 | Guertin et al. | |
| 2012/0251275 A1 * | 10/2012 | Malin | G01N 35/0099 211/59.4 |
| 2013/0109007 A1 * | 5/2013 | Akra | C12M 21/08 435/375 |
| 2013/0119284 A1 | 5/2013 | Fukano et al. | |
| 2016/0002583 A1 * | 1/2016 | Hlinka | C12M 23/34 435/305.2 |
| 2018/0016540 A1 * | 1/2018 | Sekine | C12M 41/34 |
| 2018/0058437 A1 | 3/2018 | Eilers et al. | |
| 2018/0371394 A1 * | 12/2018 | Ho | C12M 29/24 |
| 2020/0392449 A1 | 12/2020 | Griffin et al. | |
| 2021/0207073 A1 * | 7/2021 | Tanabe | C12M 41/08 |

FOREIGN PATENT DOCUMENTS

| | | | |
|---|---|---|---|
| DE | 102016208552 | * | 4/2017 |
| JP | 2006149232 | * | 6/2006 |
| JP | 2018139615 | * | 9/2018 |
| WO | WO-2012170878 A2 | | 12/2012 |

OTHER PUBLICATIONS

CableTiesAndMore. "Braided Cable Sleeving". Dec. 24, 2017. Retrieved Dec. 11, 2021 from WebArchive. https://web.archive.org/web/20171224205238/https://www.cabletiesandmore.com/BraidedSleeving.php (Year: 2017).*

* cited by examiner

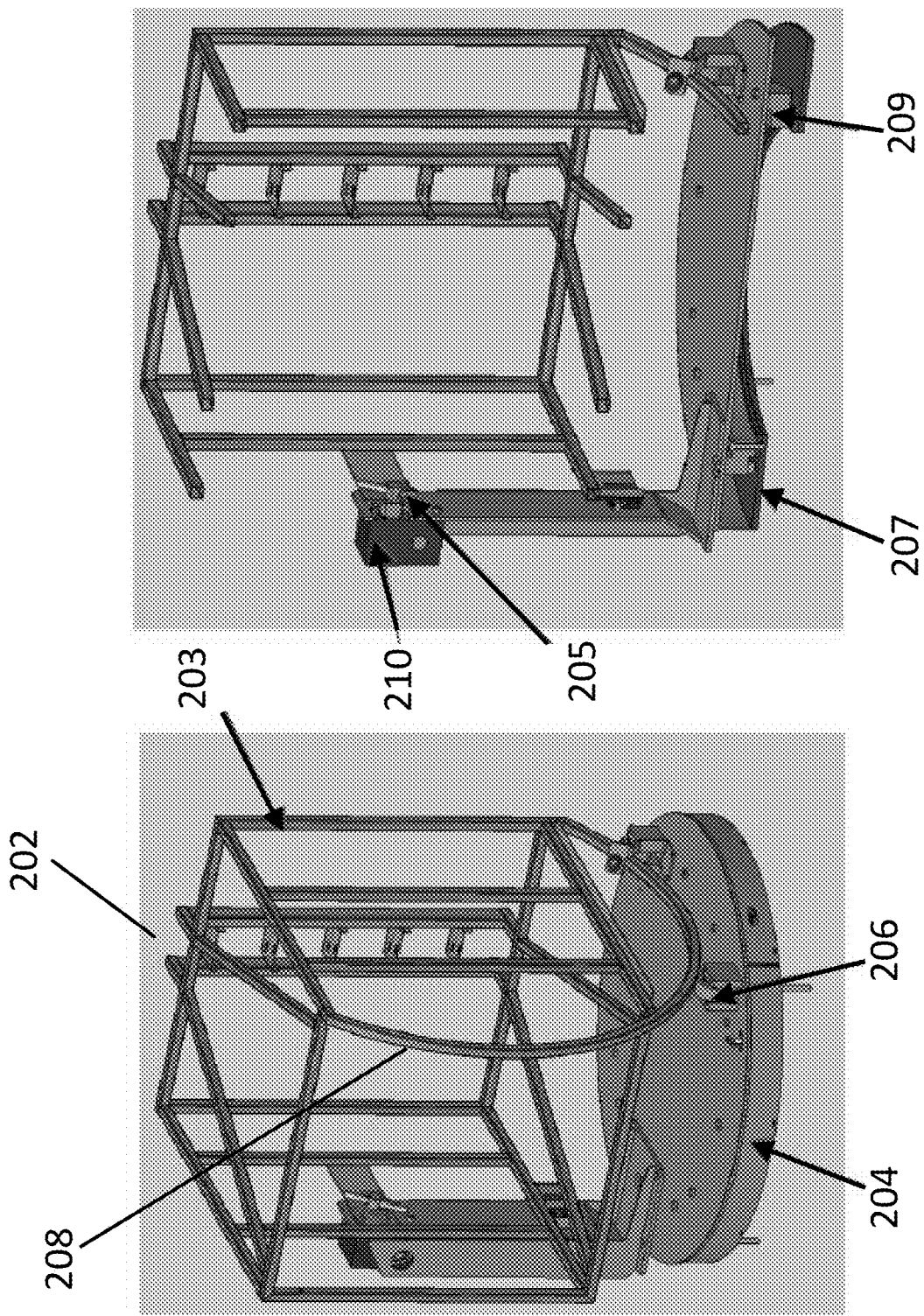

DRAWER SYSTEM FOR CULTIVATING TISSUE

RELATED APPLICATIONS

This disclosure claims benefit of and priority to U.S. provisional patent application No. 62/849,485, filed May 17, 2019. The entire disclosure, in its entirety, is herein incorporated by reference.

BACKGROUND

There is a considerable need for tissue, e.g., vascular grafts, when the patient's own tissue is unavailable (e.g., damaged, diseased). When autologous tissue is not available, often times synthetic material is used (e.g., synthetic polytetrafluoroethylene (PTFE) for blood vessels). Other types of grafts, such as decellularized bovine tissue, and human allograft tissue, for example, from cadavers, can be used, but are prone to problems (e.g., in the case of blood vessels, aneurysm, calcification, and thrombosis). Thus, there is a need in the art for devices, systems, and methods configured to produce cost-effective tissue engineered constructs that can function long term, with minimal to no side effects, in vivo.

SUMMARY OF SOME OF THE EMBODIMENTS OF THE DISCLOSURE

Exemplary embodiments of the present disclosure are directed to systems, apparatuses, and methods for cultivating and mass-producing tissue for use in humans/mammals.

In some embodiments, a bioreactor system is provided which comprises a drawer cage, housing or frame (such terms being used interchangeably throughout), at least one drawer arranged within the drawer cage, where each drawer can be configured to contain a plurality of bioreactors for cultivating biological matter, and a platform upon which the drawer cage is positioned. The platform can include a first axis upon which the drawer cage rotates or tilts thereon.

Such embodiments may include one and/or another (e.g., a plurality of, and in some embodiments, all of) of the following features, structure, functionality, or clarifications (as the case may be), leading to yet further embodiments:
- at least one fixture attached to at least one of the drawer cage and rotatable platform, where at least one of the housing and turntable can be configured to rotate or tilt via the at least one fixture along a second axis;
- a housing to house at least the drawer cage;
- the second axis is different from the first axis, such that the cage can rotate or tilt along the second axis;
- an environmental control system which, in some embodiments, can be configured to maintain any one or more of drawer cage, and the at least one drawer at a predetermined temperature, humidity, and/or pressure;
- the at least one drawer can comprise a plurality of drawers, where the system can further comprise an environmental control system which can be configured to maintain each drawer at a respective predetermined temperature, humidity and/or pressure;
- one or more organized fluid communication tubes configured to deliver one or more fluids to at least one of the drawer cage and to the at least one drawer;
- a fluid management system;
- the drawer cage can be arranged so as to receive the at least one drawer in a stacked vertical, horizontal, or oblique angle;
- the at least one drawer comprises: two (2) drawers, three (3) drawers, four (4) drawers, five (5) drawers, six (6) drawers, seven (7) drawers, eight (8) drawers, nine (9) drawers, or ten (10) drawers;
- the rotatable/tilt functionality is configured such that different areas of the cage can be accessed from a single access point;
- the drawer cage can be contained within a housing, and the single access point can correspond to an opening/door of the housing;
- at least one of rollers, slides, gears, and wheels, one or more of which can be configured to enable at least one of the platform and fixture to rotate and/or tilt;
- the angle of the rotation/tilt of the drawer cage along the first axis is between about 0° and about 360°, 0° and about 180°, or between 0° and about 90°, and angles therebetween, including, for example, 0° and 10°, 0° and 20°, 0° and 30°, 0° and 40°, 0° and 50°, 0° and 60°, 0° and 70°, 0° and 80°, 0° and 90°, 90° and 110°, 90° and 120°, 90° and 130°, 90° and 140°, 90° and 150°, 90° and 160°, 90° and 170°, 90° and 180°, 90° and 360°, 0° and 90°, 0° and 180°, 0° and 360°, or 90° and 360;
- the angle of the rotation/tilt of the drawer cage along the second axis is between about 0° and about 360°, 0° and about 180°, or between 0° and about 90°, and angles therebetween, including, for example, 0° and 10°, 0° and 20°, 0° and 30°, 0° and 40°, 0° and 50°, 0° and 60°, 0° and 70°, 0° and 80°, 0° and 90°, 90° and 110°, 90° and 120°, 90° and 130°, 90° and 140°, 90° and 150°, 90° and 160°, 90° and 170°, 90° and 180°, 90° and 360°, 0° and 90°, 0° and 180°, 0° and 360°, or 90° and 360
- at least one lock configured for locking rotation of the drawer cage along at least one of the first axis and the second axis, where (in some embodiments):
  - locking can be configured to occur at one or more angles of rotation; and/or
  - the lock can be configured to prevent rotation along the first and/or second axis and allow the at least one drawer to open
- the at least one drawer comprises a plurality of drawers, and the drawer cage can be configured to allow only a single drawer to open at a time;
- at least one motor configured to rotate the drawer cage along at least one of the first and second axes;
- one or more sensors for sensing at least one of: an open drawer, rotation along the first and/or second axes;
- a controller, configured to control the drawer cage, where the control comprises at least one of: rotating, allowing rotation of at least the drawer cage along at least one the first and second axis, opening of a drawer, and allowing opening of a drawer;
- at least one tube organizer configured to at least one of arrange and direct a plurality of tubes within at least one of the at least one drawer and, upon the at least one drawer comprising a plurality of drawers, among the plurality of drawers:
  - the at least one tube organizer can be arranged and configured to allow at least one end of the at least one drawer to be moved relative the fixed position without affecting flow in the plurality of tubes; and/or
  - the at least one drawer includes a tray configured to organize the plurality of bioreactors arranged therein:

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The above-noted embodiments will become even more evident by reference to the following detailed description and accompanying drawings.

BRIEF DESCRIPTION OF THE DRAWINGS

The skilled artisan will understand that the drawings of this disclosure are primarily for illustrative purposes and are not intended to limit the scope of inventive subject matter described herein. The drawings are not necessarily to scale; and in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A-E show example features of aspects of the drawer cage configured for placement within an incubator shell and for receiving one or more drawers, according to some embodiments.

DETAILED DESCRIPTION OF SOME OF THE EMBODIMENTS

Figure 1A:
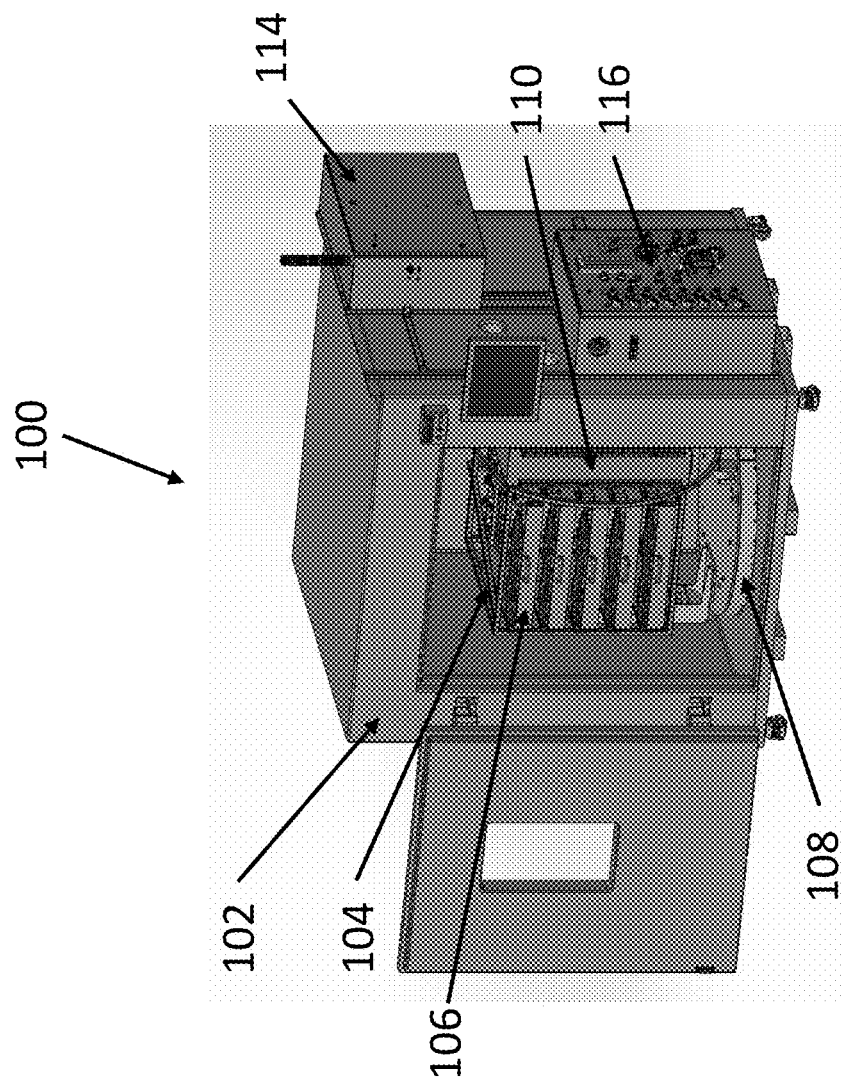
FIGS. 1A-C show example embodiment of a tissue cultivating system or an incubator used for producing human acellular vessels (HAVs) that can be used to replace diseased or damaged blood vessels in patients, according to some embodiments.
Figure 1B:
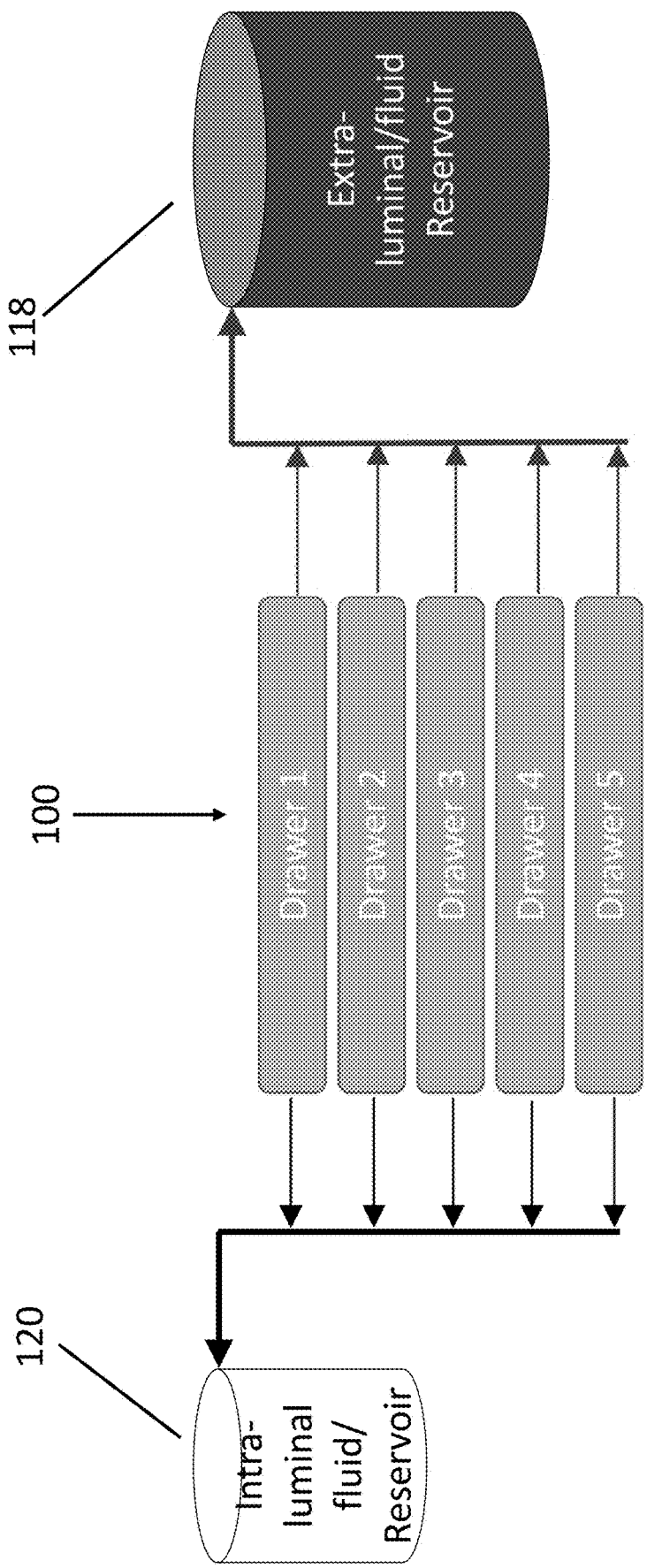
Figure 1C:
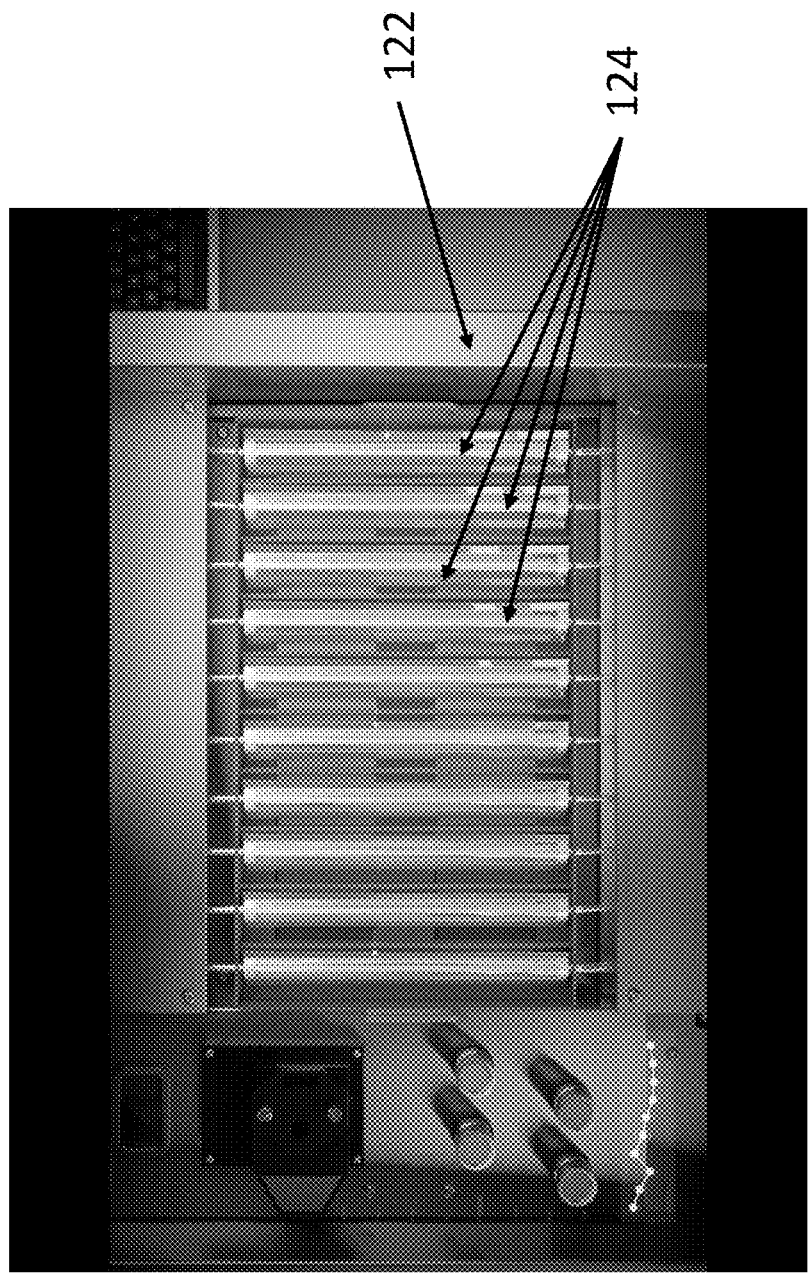
Figure 2D:
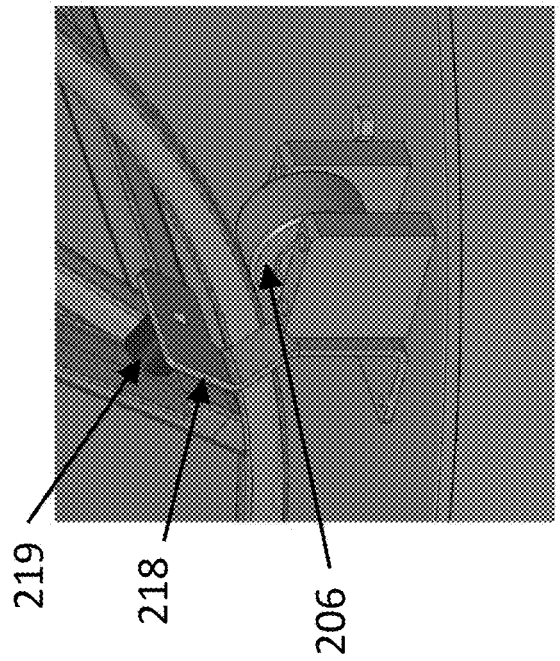
Figure 2E:
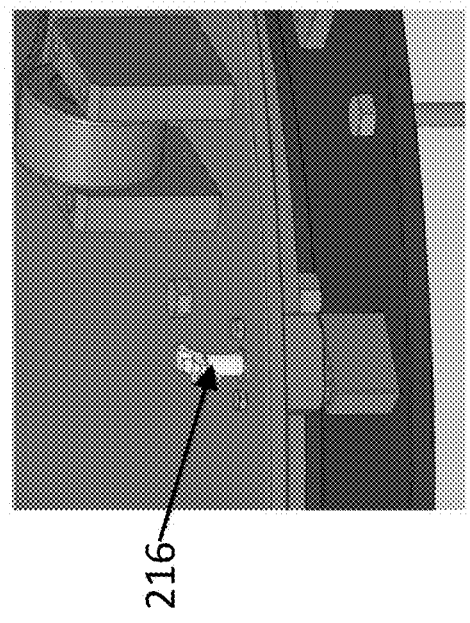
Figure 2C:
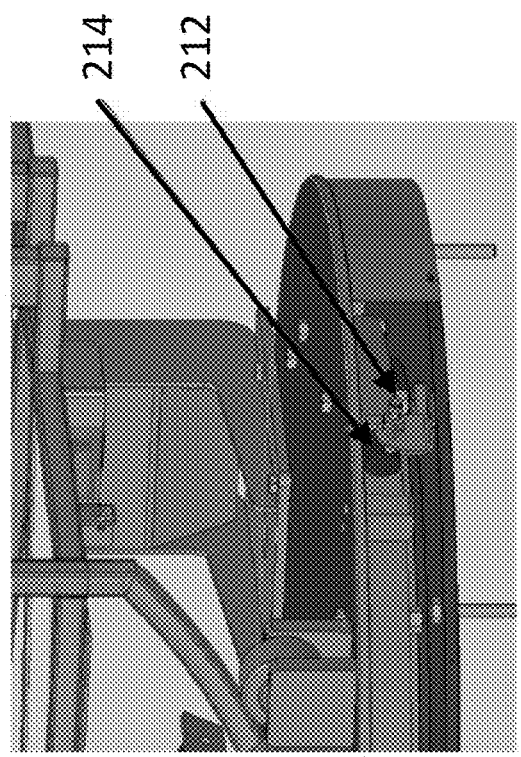

FIGS. 1A-C show example embodiments of a tissue cultivating system for producing tissue. In some embodiments, the system may be used to produce human acellular vessels (HAVs) that can be used to replace diseased or damaged blood vessels in patients. Specifically, and again for example, blood vessels damaged as a result of complications caused by various diseases or caused by trauma can be replaced by HAVs.

Accordingly, in some embodiments, incubator 100 includes an incubator shell 102, having an access opening, which may include a door, a drawer cage 104 which may be positioned within the incubator shell 102 and may be configured for receiving one or more drawers 106. Drawer cage 104 may also include a rotatable platform 108, which can be configured for rotating the drawer cage, as well as a fixture/means to enable the platform to tilt/rotate along another axis.

The flow of one or more fluids through the drawers 106 can be controlled by a materials/fluid management module (MFMM) 110 that is coupled to the drawer cage 104 (e.g., including being physically attached to the drawer cage) and includes pumps (e.g., peristaltic pumps), sensors (e.g., pressure, flow, temperature sensors), tubes, pneumatic connections for facilitating the transfer of fluids within the drawers, electrical components and connections for powering the electronics onboard and/or communicating with controller modules (e.g., external or onboard the incubator), and the like. In some embodiments, the incubator 100 may also include an environmental control module or system that facilitates the management of the incubator's environmental characteristics, including but not limited to temperature, humidity, pressure, etc. For example, the system may include incubator connections that facilitate the heating, cooling, humidifying, dehumidifying, increasing pressure and/or decreasing pressure of the incubator.

In some embodiments, the incubator 100 may include a controller module 114 that allows a user to interface with and control the incubator. For example, the controller module 114 may be coupled to the incubator (e.g., including being physically attached to the incubator shell 102) and may include a human machine interface (HMI), including (for example), a graphical user interface (GUI) that is configured to allow a user such as an incubator technician, an HAV production worker, etc., to interact with the incubator 100 (e.g., input instructions/data and/or receive data back from the incubator, with the instructions/data including but not limited to incubator status, internal parameters such as pressure, temperature, etc.). In some embodiments, the controller module 114 may also include a programmable logic controller (PLC) or distributed control system (DCS) that is configured to facilitate the automation of the HAV production process by the incubator. In some embodiments, the controller module 114 may be configured to communicate wirelessly and/or in a wired setting.

In some embodiments, the incubator 100 may also include a materials management module (MMM) 116 that is configured to manage the flow of media in the incubator, the drawers, and/or among one or more bioreactors arranged within each drawer, and in some embodiments, between the forgoing and media reservoirs 118, 120. Media reservoirs can be configured with fluid media that may include one or more dissolved gases, elements, nutrients and the like (the fluid may be a liquid or an air/gas flow). The MMM 116 may be coupled (e.g., including being physically attached) to the outside frame of the incubator shell 102, but it can be located anywhere proximate the incubator and may be fluidly connected thereto (as well as fluidly connected to the drawers and/or bioreactors). FIG. 1C, in particular, shows an example embodiment of a drawer for inclusion with the drawer cage. As shown, drawer 122, according to some embodiments, can include one or more (and preferably a plurality) of bioreactor systems ("bioreactors") 124 and components associated therewith.

FIGS. 2A-E shows example features of aspects of the drawer cage 202, which can be configured as an assembly of rigidly connected supports 203 (for example), the cage being configured for placement within the incubator shell, for receiving one or more drawers, according to some embodiments. The platform which, according to one and/or another of some of the embodiments, may be configured for at least one of tilting and/or rotating the drawer cage along one or more axes. As noted above, in some embodiments, each drawer cage may be configured to receive one or more drawers. For example, the drawer cage can be configured to receive the drawers in either a vertically or horizontal stacked arrangement, or even at any angle therebetween. In some embodiments, any number of drawers can be received by the cage, including but not limited to, a single drawer, 2 drawers, 3 drawers, 4 drawers, 5 drawers, 6 drawers, 7 drawers, 8 drawers, 9 drawers, 10 drawers, etc.

The rotatable and/or tilt functionality can be configured to allow the cage to be maneuvered around one or more axes such that different areas of the cage can be accessed from an opening/door of the incubator shell. Also, such can be configured to allow a specific tilting of the cage to any angle (or between a range of angles). For example, the rotatable platform 204 may rotate about an axis perpendicular to its surface (i.e., vertical along the height of the drawer cage 202), thereby rotating the drawer cage 202 (and drawers contained therein) about the same perpendicular axis. In some embodiments, the drawer cage 202 may be positioned atop the rotatable platform via one or more fixtures that facilitate the rotation/tilt of the drawer cage about an axis different than the axis perpendicular to the plane of the rotatable platform. For example, the one or more tilting fixtures configured as support rollers 206 are configured to allow at least part of the drawer cage (e.g., a hollow structure section (HSS) 208 serving as an edge of the drawer cage) to roll or slide over the roller 206, thereby resulting in the rotation/tilting of the drawer cage by an angle measured from the axis perpendicular to the plane of the rotatable platform 204. The rotatable platform 204 can include, in some embodiments, a bottom portion 207, upon which an inner ring 209, for example, may rides/rotate thereon (e.g., which can include rollers and the like, as well as a motor, and/or can comprise a motor).

For example, in some embodiments, the angle of the rotation/tilt of the drawer cage 202 may be up to 360 degrees, or any ranges and subranges of rotation and/or tilt therebetween (e.g., measured from the axis perpendicular to the plane of the rotatable platform). In some embodiments, the rotatable platform 204 may or may not be rotating or moving when a section of the drawer cage such as the edge 208 rolls or slides over the fixture 206 and causes the rotation or tilting of the drawer cage 202 itself. In some embodiments, the rotation of the rotatable platform 204 about the perpendicular axis and the rotation and/or tilting of the drawer cage 202 by some amount of angle as measured from the same axis may occur at different times or at least substantially the same time.

In some embodiments, the rotation of the rotatable platform 204 and/or the rotation and/or tilt of the drawer cage 202 may be done manually, or may be automated and/or motorized/powered by a motor drive 210 coupled to the drawer cage 202 and controlled by and/or including a motor drive assembly, which can include portion 205, which, in some embodiments, can be configured to enable connection of the motor to the cage, for example, as well as other possible functions (in addition to or in the alternative). In some embodiments, the drawer cage 202 may include a rotation sensor 212/214 which may be configured to provide a signal/information to the tilt motor drive to prevent rotations of the rotatable platform 204 and/or the drawer cage 202 when the rotations are faulty, or, for according to a present amount of rotation/tilt. Such can be configured with a controller/processor which is configured to control powered tilt/rotation of the cage using, for example, information from the sensor. For example, in some embodiments, the rotatable platform 204 may not have rotated by a first desired angle, in which case the sensor 212/214 signals the motor drive to prevent the rotation and/or tilting of the drawer cage 202 until the platform 204 rotates by the desired angle (or reverses to its resting position). In some embodiments, the reverse can occur where the drawer cage may not have rotated and/or tilted by a second desired angle, in which case the sensor 212/214 prevents the motor drive from rotating the rotatable platform 204 until the drawer cage 202 rotates and/or tilts by the desired angle. In some embodiments, the rotatable platform 204 may include a lock feature 216 that allows for the manual control of the rotations/tilts of the rotatable platform 204 and/or the drawer cage 202. An example of such a lock feature is a rotation lock pin. For example, the rotation lock pin can be manually removed from the rotatable platform 204 to allow the rotation of the drawer cage 202 until the drawer cage 202 attains the correct position, at which point it can be inserted back in to maintain the cage assembly in place. Other components can include a structural member(s) 218 which includes element 219, the each such element, or a combination thereof, can be configured to, in some embodiments, to act as a stop and/or a guide for the cage to protect against over-rotation (in some embodiments).

Figure 3:
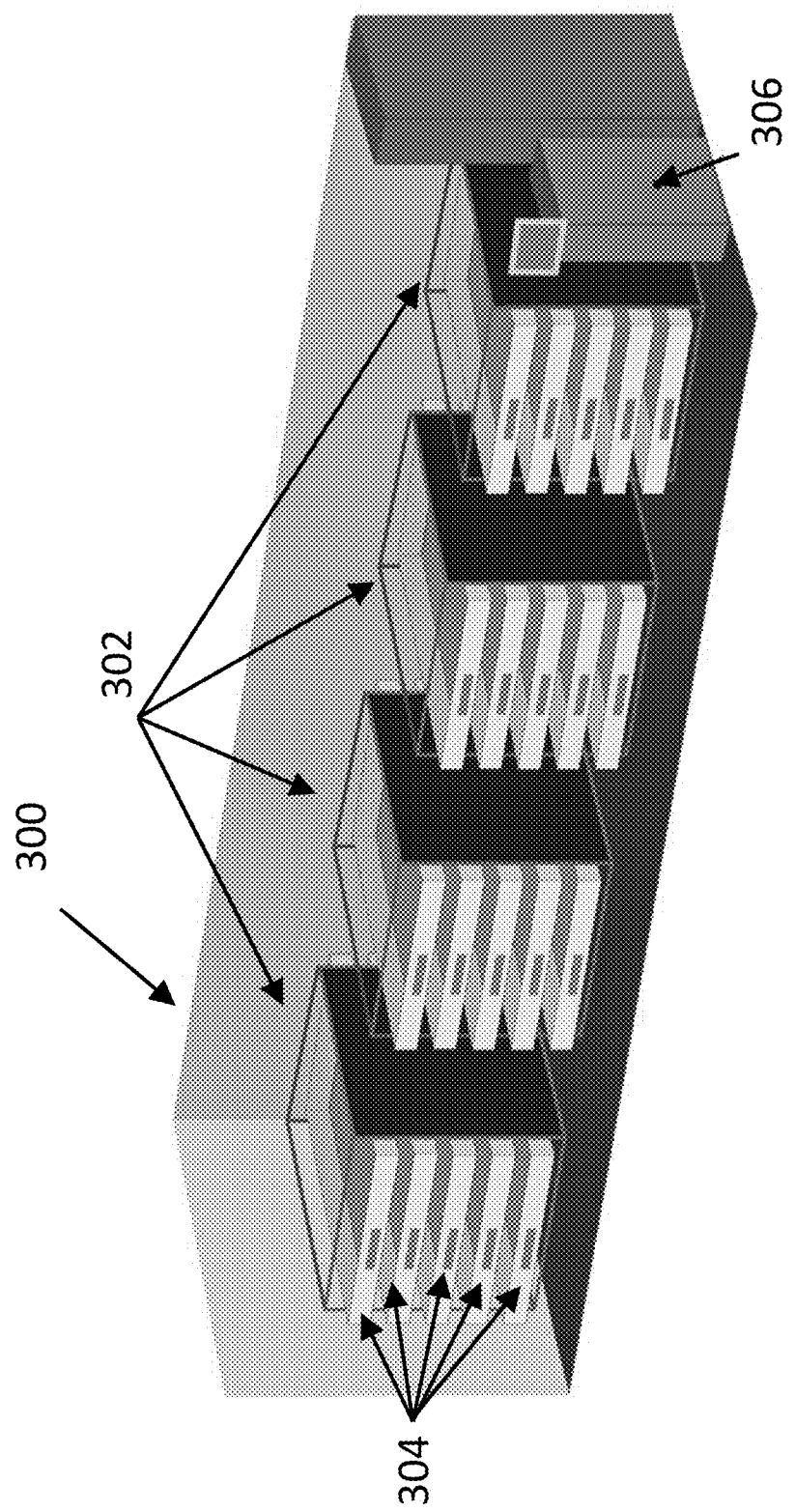
FIG. 3 shows a perspective view of an embodiment of a tissue cultivating system, according to some embodiments of the disclosure.

FIG. 3 shows an example embodiment of a multi-tiered platform 300 including a plurality of incubators 302, which may share one or more common reservoirs, according to some embodiments. As discussed above, in some embodiments, a plurality of drawers 304 can be included within each incubator shell, and the drawers can be coupled to a common set of reservoirs (e.g., biomedia reservoir, intraluminal fluid reservoir, etc.) that provide biomedia, fluids, gases, etc., from a common source. In some embodiments, one, a plurality, or all of the drawers can also share a common MMM 306. Thus, in some embodiments, a plurality of incubators can be arranged in parallel to form a multi-tiered platform that is configured to allow for a simultaneous or near simultaneous production of large quantities of tissue (e.g., HAVs) while maintaining a reduced manufacturing footprint.

In some embodiments, the multi-tiered platform allows for consistent and reliable production of HAVs as each bioreactor is likely to be exposed to at least substantially similar environmental and/or fluid conditions including but not limited to temperature, amount and type of dissolved gases, nutrients, fluid flow rates, and/or the like. Further, the parallel arrangement of the incubators facilitates the sequential addition of biomedia, fluids, gases, etc., to all the incubators/drawers/bioreactors in parallel, if desired. Thus, and as noted earlier, the flow path for biomedia, fluids, gases, etc., circulating through the multi-tiered platform can be configured to be in serial, in parallel, or a hybrid of the two, allowing for enhanced control in how the HAVs are produced. In some embodiments, the multi-tiered platform allows for the change of tunable amount of cell culture media from the multi-tiered platform system at predetermined intervals.

Control of various embodiments of tissue cultivating systems disclosed herein, as well as one or more components and/or sub-systems thereof (and the making of HAVs for example) can be accomplished via hardware, software or a combination thereof. When implemented in software, the software code can be executed on any suitable processor or collection of processors, whether provided in a single computer or distributed among multiple computers.

Typically, such systems are controlled by one or more computer programmable processors (either AISC or via software) having one or more applications running thereon which operate one or more (and preferably all) of the pumps, motors, sensors, valves, clamps of the tissue cultivating systems disclosed herein. To this end, and as noted, one or more sensors can be provided to collect information (e.g., sense a condition) for any component and sub-system of the disclosed tissue cultivating systems which allow the controller to perform the cultivating process as so desired.

Accordingly, the controller/computer may be embodied in any of a number of forms, such as a rack-mounted computer, a desktop computer, a laptop computer, or a tablet computer (i.e., processor), server, and the like. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface which can be used to at least one of program, operate, and monitor the embodiments disclosed herein. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such controllers/computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

In some embodiments, the platform is advantageous for any one or more of the following reasons:
  allows for tissue growth and de-cellularization to occur on the same system, so as to greatly reduces the number of aseptic manipulations of components;
  maximizes removal of residual fluid during bioreactor draining (e.g., promotion of the removal of residual cellular material during bioreactor drains);
  enables an operator to access a drawer to load bioreactors and associated components (e.g., tubing);
  and/or
  allows access to mechanical components (pumps, valves, sensors, etc.), e.g., for functional verifications, calibrations, and routine maintenance.

Various inventive concepts disclosed here may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety.

As noted elsewhere, the disclosed inventive embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to binding event determinative systems, devices and methods. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore, represent patentable subject matter and are distinguishable therefrom (i.e., claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined. i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B): in another embodiment, to B only (optionally including elements other than A): in yet another embodiment, to both A and B (optionally including other elements): etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A): in yet another embodiment, to at least one, optionally including more than one, A, and at least one, optionally including more than one, B (and optionally including other elements): etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A bioreactor system, comprising:
   an enclosure;
   a platform having a planar surface;
   a mount extending from and orthogonal to the planar surface, the mount comprising a motor drive;
   a bioreactor array housing arranged within the enclosure and supported on the planar surface of the platform by a first edge on a first side of the bioreactor array housing, the first edge comprising a straight section and a curved section to passively permit constrained rotation of the bioreactor array housing, the curved section of the first edge of the bioreactor array housing being in contact with a bearing surface on the planar surface of the platform, the bioreactor array housing further comprising a fixture on a second side of the bioreactor array housing, the fixture being coupled to the motor drive on the mount; and
   at least one bioreactor array comprising a plurality of bioreactors arranged within the bioreactor array housing, each bioreactor of the at least one bioreactor array being configured for cultivating vascular grafts;
   wherein the platform is configured to rotate about a first axis that is perpendicular to the planar surface of the platform,
   wherein the bioreactor array housing is configured to rotate about the first axis and rotate about a second axis defined by the planar surface of the platform via the fixture and the curved section of the first edge of the bioreactor array housing, the second axis being orthogonal to the first axis, and
   wherein the platform and the bioreactor array housing are independently rotatable.

2. The system of claim 1, wherein the enclosure is an incubator.

3. The system of claim 1, further comprising an environmental control system configured to maintain at least one of the bioreactor array housing and the at least one bioreactor array at one or more of a predetermined temperature, a predetermined humidity, and a predetermined pressure.

4. The system of claim 1, further comprising an environmental control system,
   wherein the environmental control system is configured to maintain each bioreactor array of the at least one bioreactor array at a respective one or more of a predetermined temperature, a predetermined humidity, and a predetermined pressure.

5. The system of claim 1, further comprising one or more fluid communication tubes configured to deliver one or more fluids to at least one of the bioreactor array housing and the at least one bioreactor array therein.

6. The system of claim 1, further comprising a fluid management system attached to the bioreactor array housing and including pumps, sensors, and fluid communication tubes configured to independently deliver media to each bioreactor of the plurality of bioreactors of the at least one bioreactor array.

7. The system of claim 6, wherein the at least one bioreactor array is a plurality of bioreactor arrays, and media is sequentially provided to a first bioreactor array and to a second bioreactor array in parallel.

8. The system of claim 1, wherein the bioreactor array housing is arranged so as to receive the at least one bioreactor array in a stacked arrangement and at one or more of a vertical, a horizontal, or an oblique orientation.

9. The system of claim 1, wherein the at least one bioreactor array comprises: two (2) bioreactor arrays, three (3) bioreactor arrays, four (4) bioreactor arrays, five (5) bioreactor arrays, six (6) bioreactor arrays, seven (7) bioreactor arrays, eight (8) bioreactor arrays, nine (9) bioreactor arrays, or ten (10) bioreactor arrays.

10. The system of claim 1, wherein the platform is configured to rotate such that different areas of the bioreactor array housing can be accessed from a single access point.

11. The system of claim 10,
    wherein the at least one bioreactor array and the platform are within the enclosure,
    wherein the enclosure is an incubator, and
    wherein the bioreactor array housing is contained within the incubator and the single access point corresponds to an opening or door of the incubator.

12. The system of claim 1, further comprising at least one of rollers, slides, gears, and wheels, wherein one or more of the rollers, slides, gears, and wheels is configured to enable at least one of the platform and the at least one fixture to rotate.

13. The system of claim 1, wherein the rotation of the platform and/or the bioreactor array housing about the first axis is between about 0° and 10°, or between about 0° and 20°, or between about 0° and 30°, or between about 0° and 40°, or between about 0° and 50°, or between about 0° and 60°, or between about 0° and 70°, or between about 0° and 80°, or between about 0° and 90°, or between about 90° and 110°, or between about 90° and 120°, or between about 90° and 130°, or between about 90° and 140°, or between about 90° and 150°, or between about 90° and 160°, or between about 90° and 170°, or between about 90° and 180°, or between about 90° and 360°, or between about 0° and 180°, or between about 0° and 360°, or between about 90° and 360°.

14. The system of claim 1, wherein the rotation of the platform and/or the bioreactor array housing about the second axis is between about 0° and 10°, or between about 0° and 20°, or between about 0° and 30°, or between about 0° and 40°, or between about 0° and 50°, or between about 0° and 60°, or between about 0° and 70°, or between about 0° and 80°, or between about 0° and 90°, or between about 90° and 110°, or between about 90° and 120°, or between about 90° and 130°, or between about 90° and 140°, or between about 90° and 150°, or between about 90° and 160°, and/or between about 90° and 170°.

15. The system of claim 1, further comprising at least one lock configured for locking the rotation of the bioreactor array housing about the first axis and/or the second axis.

16. The system of claim 15, wherein locking is configured to occur at one or more angles of rotation.

17. The system of claim 15, wherein the lock is configured to prevent rotation about the first axis or the second axis and allow the at least one bioreactor array to be accessible.

18. The system of claim 1, wherein the at least one bioreactor array comprises two or more bioreactor arrays and the bioreactor array housing is configured to allow only a single bioreactor array to be accessible at a time.

19. The system of claim 1, further comprising one or more sensors for sensing at least one of: an accessed bioreactor array, rotation about the first axis, and rotation about the second axis.

20. The system of claim 1, further comprising a controller configured to control rotation of the bioreactor array housing.

21. The system of claim 20, wherein controlling the bioreactor array housing comprises at least one of:
rotating;
allowing rotation of at least the bioreactor array housing about at least one of the first axis and the second axis;
accessing the at least one bioreactor array; and
allowing access to the at least one bioreactor array.

22. The system of claim 1, further comprising at least one tube organizer configured to arrange and/or direct one or more fluid communication tubes.

23. The system of claim 22, wherein the at least one tube organizer is arranged and configured to allow at least one end of the at least one bioreactor array to be moved relative to a fixed position without affecting flow in the one or more fluid communication tubes.

24. The system of claim 1, wherein the at least one bioreactor array includes a tray configured to organize the plurality of bioreactors arranged therein.

25. The system of claim 1, wherein the planar surface of the platform comprises an aperture configured to receive a locking pin, the locking pin configured to engage the bioreactor array housing to permit or cease rotation of the bioreactor array housing.

26. The system of claim 1, wherein the bioreactor array housing further comprises a stop arranged on the curved section of the first edge of the bioreactor array housing and configured to prevent over-rotation of the bioreactor array housing.

* * * * *